United States Patent

Katsuda et al.

Patent Number: 6,107,339
Date of Patent: *Aug. 22, 2000

[54] DERIVATIVE OF ESTER OF CARBOXYLIC ACID, AND INSECTICIDE AND INSECT PROOFING AGENT CONTAINING THE SAME

[75] Inventors: Yoshio Katsuda, Nishinomiya; Koji Nakayama; Yoshihiro Minamite, both of Toyonaka, all of Japan

[73] Assignee: Dainihon Jochugiku Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/722,029

[22] PCT Filed: Feb. 7, 1996

[86] PCT No.: PCT/JP96/00254

§ 371 Date: Nov. 1, 1996

§ 102(e) Date: Nov. 1, 1996

[87] PCT Pub. No.: WO96/24573

PCT Pub. Date: Aug. 15, 1996

[30] Foreign Application Priority Data

Feb. 7, 1995 [JP] Japan ................................. 7-054936

[51] Int. Cl.$^7$ .................................................. A01N 53/00
[52] U.S. Cl. ........................ 514/531; 514/461; 514/464; 549/447; 549/500; 560/124
[58] Field of Search ............................ 560/124; 549/447, 549/500; 514/531, 461, 464

[56] References Cited

U.S. PATENT DOCUMENTS

| | | | |
|---|---|---|---|
| 2,458,656 | 1/1949 | Synerholm | 260/338 |
| 2,886,485 | 5/1959 | Barthel | 167/33 |
| 3,673,215 | 6/1972 | Vollrath | 560/124 |

(List continued on next page.)

FOREIGN PATENT DOCUMENTS

| | | | |
|---|---|---|---|
| 345801 | 12/1989 | European Pat. Off. | 560/124 |
| 555153 | 8/1993 | European Pat. Off. | |
| 2-536 392 | 5/1984 | France | |
| 57-11943 | 1/1982 | Japan | |
| 59-25350 | 2/1984 | Japan | |
| 63-201146 | 8/1988 | Japan | |
| 63-267706 | 11/1988 | Japan | |
| 2-22249 | 1/1990 | Japan | |
| 5-279213 | 10/1993 | Japan | |
| 6-100499 | 4/1994 | Japan | |

OTHER PUBLICATIONS

Elliott, Chemical Society Reviews, vol. 7, pp. 473–505, 1978.
Chem. Abstr. No. 65:8974a–b, 1966.

*Primary Examiner*—Michael L. Shippen
*Attorney, Agent, or Firm*—Oliff & Berridge, PLC

[57] ABSTRACT

The derivatives of esters of carboxylic acids represented by the general formula I:

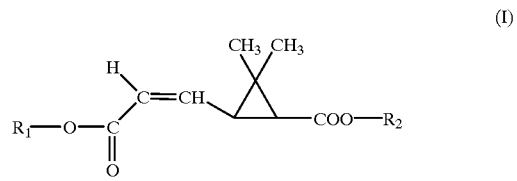

wherein:
  $R_1$ is an alkyl group having a chain or branched chain of 1 to 4 carbon atoms; and
  $R_2$ is a group represented by the following general formulae II, III or IV;

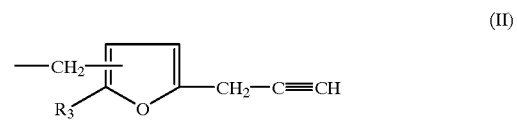

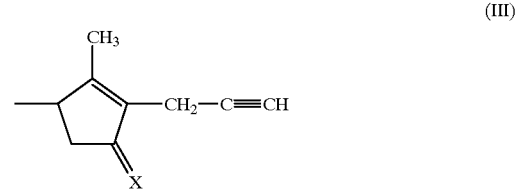

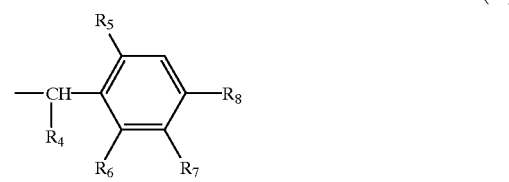

wherein:
  $R_3$ is a hydrogen atom or a methyl group;
  X is an oxygen atom or a methylidene group;
  $R_4$ is an hydrogen atom or an ethynyl group;
  $R_5$ and $R_6$ are alike or differently selected from the group consisting of hydrogen, fluorine, chlorine atoms or methyl group;
  $R_7$ is a hydrogen atom or a trifluoromethyl group;
  $R_8$ is selected from the group consisting of propargyl, methoxymethyl or methylthio groups; or
  $R_7$ and $R_8$ may combine with each other to form a methylenedioxy chain; and the process for manufacturing the same, and the insecticides and the insect proofing agents containing the same as an active ingredient.

The compounds represented by the general formula I are useful ingredients of insecticides and insect proofing agents which have both a fast-acting property and a lethal effect, and moreover, are highly safe to mammals; and therefore, insecticides and insect proofing agents containing the above compounds have a highly practical use.

12 Claims, No Drawings

U.S. PATENT DOCUMENTS

| | | | |
|---|---|---|---|
| 3,795,696 | 3/1974 | Katsuda | 560/124 |
| 4,024,163 | 5/1977 | Elliott | 560/124 |
| 4,370,346 | 1/1983 | Punja | 560/124 |
| 4,405,640 | 9/1983 | Punja | 560/124 |
| 4,542,142 | 9/1985 | Martel et al. | |
| 4,689,342 | 8/1987 | Tessier | 560/124 |
| 4,808,749 | 2/1989 | Martel | 560/124 |
| 4,833,163 | 5/1989 | Martel | 560/124 |
| 4,939,172 | 7/1990 | Cadiergue | 560/124 |
| 5,019,595 | 5/1991 | Yano | 560/124 |
| 5,026,862 | 6/1991 | Tessier | 560/124 |
| 5,312,964 | 5/1994 | Babin | 560/124 |
| 5,420,159 | 5/1995 | Babin | 560/124 |
| 5,550,258 | 8/1996 | Iwasaki | 560/124 |

DERIVATIVE OF ESTER OF CARBOXYLIC ACID, AND INSECTICIDE AND INSECT PROOFING AGENT CONTAINING THE SAME

TECHNICAL FIELD

The present invention relates to novel derivatives of esters of carboxylic acids, processes for manufacturing the same, and insecticides and insect proofing agents containing the same.

BACKGROUND ART

Compounds of a natural and a synthetic pyrethroid series are widely used in the fields of agricultural use as well as home use, because they have a high insecticidal and insect proofing effect on insects and are safe to mammals. However, these activities are not entirely satisfactory to some fields. For example, aerosol spray insecticides for home use are required to contain an active ingredient having both a fast-acting property and a lethal effect, but up to now there have been no practical pyrethroids having the above property and effect at the same time. Therefore, pyrethroid having an excellent fast-acting property and fine lethal effect have been used mixed with each other. Further, in the case of a certain kind of injurious insect in an agricultural field, its resistance to pyrethroid seriously threatens to develop. Because of the above noted background, novel insecticides and insect proofing agents which are much more useful are strongly desired.

DISCLOSURE OF THE INVENTION

The present invention is made to develop a novel compound which can provide a solution to the problems the insecticides and insect proofing agents currently in use have, that is, a novel compound which has a fast-acting property and a lethal effect at the same time, and is high in safety and excellent in every point; to provide a process for manufacturing the same; and to provide insecticides and insect proofing agents which contain the same as an effective ingredient.

After concentrating their energy on this study to achieve the above objects, the present inventors have found novel derivatives of esters of carboxylic acids represented by the following general formula I:

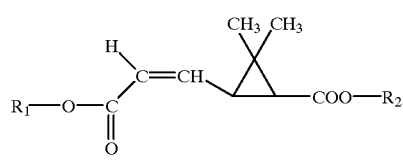

wherein:
R$_1$ is an alkyl group having a chain or branched chain of 1 to 4 carbon atoms; and
R$_2$ is a group represented by the following general formulae II, III or IV;

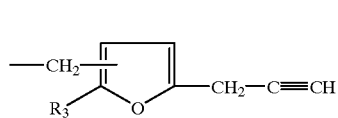

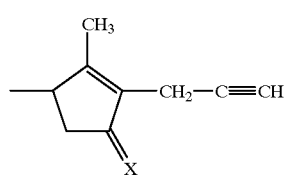

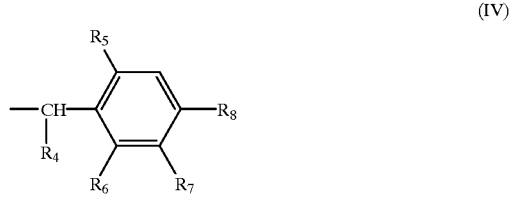

wherein:
R$_3$ is a hydrogen atom or a methyl group;
X is an oxygen atom or a methylidene group;
R$_4$ is an hydrogen atom or an ethynyl group;
R$_5$ and R$_6$ are alike or differently selected from the group consisting of hydrogen, fluorine, chlorine atoms or methyl group;
R$_7$ is a hydrogen atom or a trifluoromethyl group;
R$_8$ is selected from the group consisting of propargyl, methoxymethyl or methylthio groups; or
R$_7$ and R$_8$ may combine with each other to form a methylenedioxy chain; and confirmed that the compounds can be put to practical use, and thus perfected the present invention.

In other words, the present invention of in a first embodiment relates to novel derivatives of esters of carboxylic acids represented by the general formula I. Though there exists optical or geometrical isomers based on the steric structures of the portions of cyclopropanecarboxylic acid and alcohol among esters represented by the general formula I, all such esters are also included by the present invention.

The typical examples of novel derivatives of esters of carboxylic acids represented by the general formula I are as follows, but they are not intended to limit the present invention.

(1) Compound 1

5-propargyl-2-furylmethyl 2,2-dimethyl-3-(3-methoxy-3-oxo-1-propenyl)cyclopropanecarboxylate

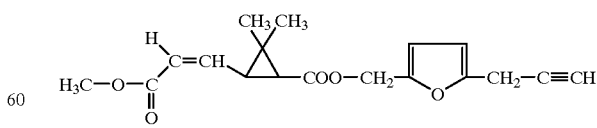

(2) Compound 2

5-propargyl-2-methyl-3-furylmethyl 2,2-dimethyl-3-(3-methoxy-3-oxo-1-propenyl)cyclopropanecarboxylate

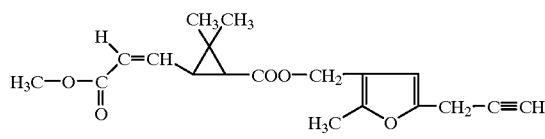

(3) Compound 3
2-methyl-3-propargyl-4-oxo-2-cyclopentene-1-yl 2,2-dimethyl-3-(3-methoxy-3-oxo-1-propenyl) cyclopropanecarboxylate

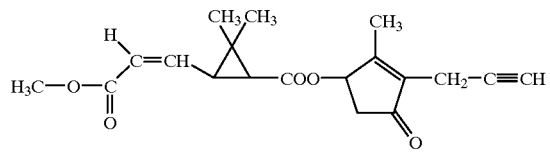

(4) Compound 4
4-propargylbenzyl 2,2-dimethyl-3-(3-methoxy-3-oxo-1-propenyl) cyclopropanecarboxylate

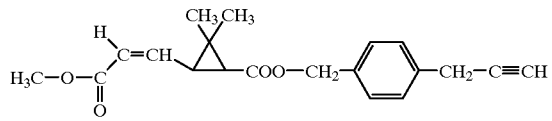

(5) Compound 5
2,6-dimethyl-4-propargylbenzyl 2,2-dimethyl-3-(3-methoxy-3-oxo-1-propenyl)cyclopropanecarboxylate

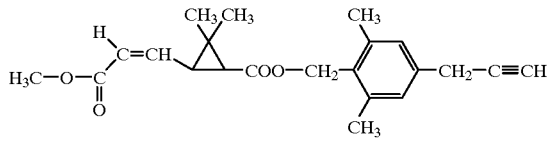

(6) Compound 6
4-methoxymethylbenzyl 2,2-dimethyl-3-(3-methoxy-3-oxo-1-propenyl)cyclopropanecarboxylate

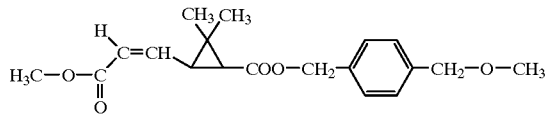

(7) Compound 7
2-fluoro-5-trifluoromethyl-α-ethynylbenzyl 2,2-dimethyl-3-(3-methoxy-3-oxo-1-propenyl) cyclopropanecarboxylate

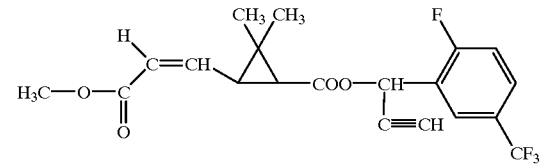

(8) Compound 8
2-methyl-3-propargyl-4-methylidene-2-cyclopentene-1-yl 2,2-dimethyl-3-(3-ethoxy-3-oxo-1-propenyl) cyclopropanecarboxylate

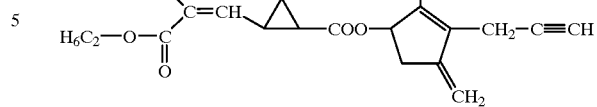

(9) Compound 9
2,6-difluoro-4-methylthiobenzyl 2,2-dimethyl-3-(3-isopropoxy-3-oxo-1-propenyl)cyclopropanecarboxylate

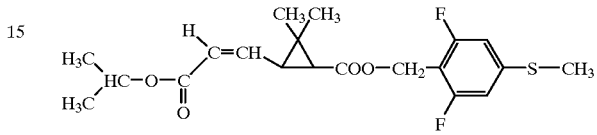

(10) Compound 10
2-chloro-4,5-methylenedioxy-α-ethynylbenzyl 2,2-dimethyl-3-(3-n-butoxy-3-oxo-1-propenyl) cyclopropanecarboxylate

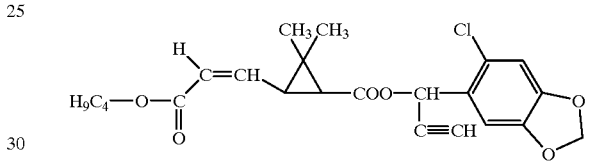

(11) Compound 11
5-propargyl-2-furylmethyl 2,2-dimethyl-3-(3-isopropoxy-3-oxo-1-propenyl)cyclopropanecarboxylate

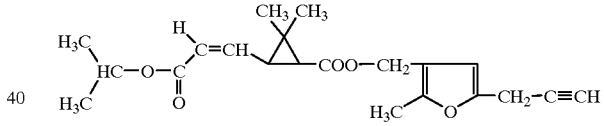

(12) Compound 12
5-propargyl-2-methyl-3-furylmethyl 2,2-dimethyl-3-(3-isopropoxy-3-oxo-1-propenyl)cyclopropanecarboxylate

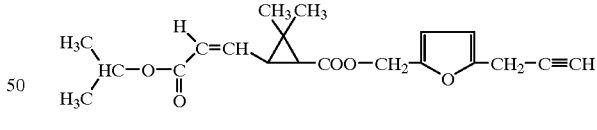

(13) Compound 13
2-methyl-3-propargyl-4-oxo-2-cyclopentene-1-yl 2,2-dimethyl-3-(3-isopropoxy-3-oxo-1-propenyl) cyclopropanecarboxylate

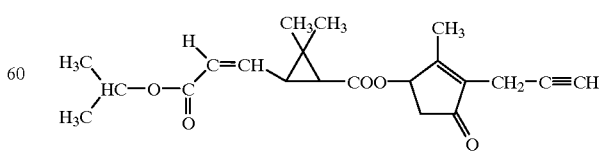

(14) Compound 14
4-propargylbenzyl 2,2-dimethyl-3-(3-ethoxy-3-oxo-1-propenyl)cyclopropanecarboxylate

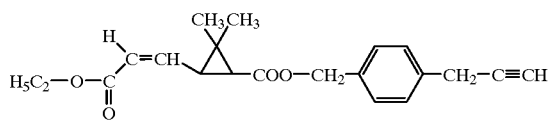

(15) Compound 15
4-methoxymethylbenzyl 2,2-dimethyl-3-(3-ethoxy-3-oxo-1-propenyl)cyclopropanecarboxylate

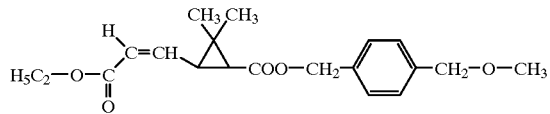

(16) Compound 16
2-fluoro-4,5-methylenedioxybenzyl 2,2-dimethyl-3-(3-n-propoxy-3-oxo-1-propenyl) cyclopropanecarboxylate

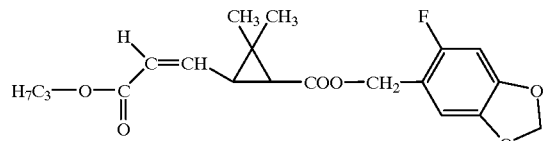

(17) Compound 17
2-chloro-4-methylthiobenzyl 2,2-dimethyl-3-(3-n-butoxy-3-oxo-1-propenyl)cyclopropanecarboxylate

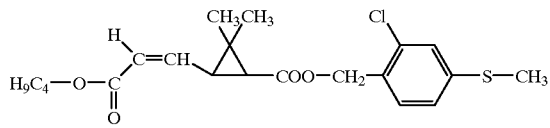

(18) Compound 18
2-chloro-5-trifluoromethyl-α-ethynylbenzyl 2,2-dimethyl-3-(3-t-butoxy-3-oxo-1-propenyl) cyclopropanecarboxylate

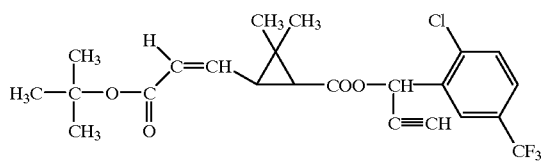

(19) Compound 19
5-propargyl-3-furylmethyl 2,2-dimethyl-3-(3-methoxy-3-oxo-1-propenyl)cyclopropanecarboxylate The present invention of in a second embodiment relates to the novel derivatives of esters of carboxylic acids of the first embodiment wherein the portion of cyclopropanecarboxylic acid has 1R, cis structure and the double bonds have a steric structure of Z configuration.

Each of a third embodiment to a embodiment of the present invention relates to a novel derivative of an ester of carboxylic acid according to the first embodiment or the second embodiment which is represented by any one of the following formulae from V to XI:

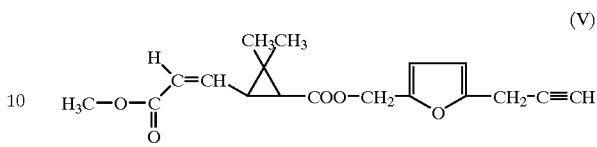
(V)

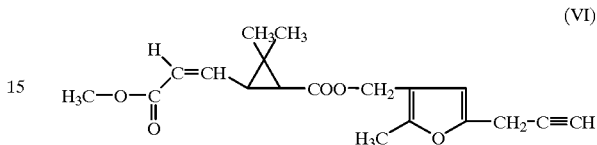
(VI)

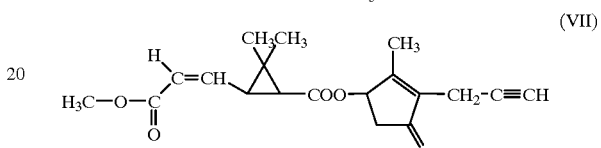
(VII)

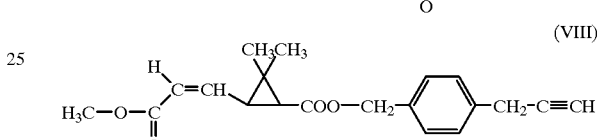
(VIII)

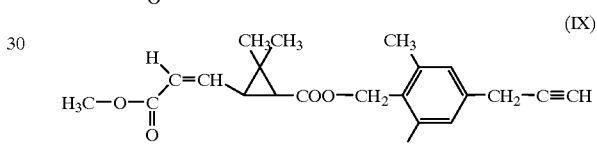
(IX)

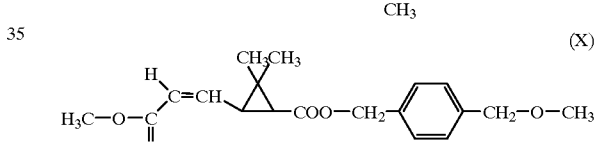
(X)

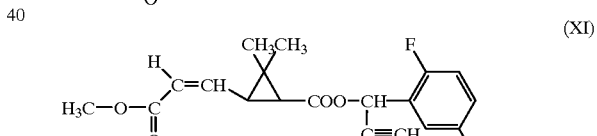
(XI)

The present invention of in a tenth embodiment relates to a step of reacting carboxylic acids having the general formula XII or their reactive derivatives with alcohols having the general formula XIII or their reactive derivatives when manufacturing the novel derivatives of esters of carboxylic acids according to the first embodiment.

The general formula XII is represented as follows:

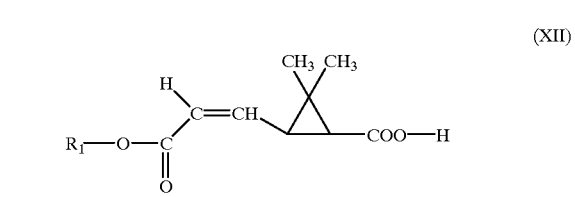
(XII)

wherein:
  $R_1$ is an alkyl group having a chain or branched chain of 1 to 4 carbon atoms.
The general formula XIII is represented as follows:

HO—R$_2$ (XIII)

wherein:

R$_2$ is a group represented by the general formulae II, III or IV;

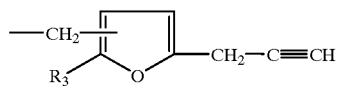
(II)

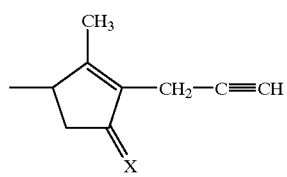
(III)

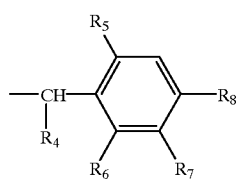
(IV)

wherein:

R$_3$ is a hydrogen atom or a methyl group;

X is an oxygen atom or a methylidene group;

R$_4$ is a hydrogen atom or an ethynyl group;

R$_5$ and R$_6$ are alike or differently selected from the group consisting of hydrogen, fluorine, chlorine atoms or methyl group;

R$_7$ is a hydrogen atom or a trifluoromethyl group;

R$_8$ is selected from the group consisting of propargyl, methoxymethyl or m,ethylthio groups; or R$_7$ and R$_8$ may combine with each other to form a methylenedioxy chain.

Reactive derivatives of carboxylic acids include, for example, acid halides, acid anhydrides, carboxylic lower alkyl esters, alkaline metal salts or their salts with organic tertiary bases. On the other hand, reactive derivatives of alcohols include, for example, chlorides, bromides, p-toluenesulfonic esters. The reaction is carried out in an appropriate solvent, in the presence of deoxidizer or organic/ inorganic base or acid as a catalyst if necessary, by heating if necessary.

According to a preferred embodiment of the present invention, carboxylic acids and alcohols are esterified in the presence of dicyclohexylcarbodiimide and 4-dimethylaminopyridine.

When esters having a preferred steric structure are manufactured, normally a more practical process is that first carboxylic acid or alcohol having a preferred steric structure is synthesized, then they are esterified; though there is a method of separating obtained esters using an optical resolution agent.

The present invention in an eleventh embodiment relates to insecticides and insect proofing agents which contain a novel derivative of an ester of carboxylic acid according to the first embodiment represented by the general formula I:

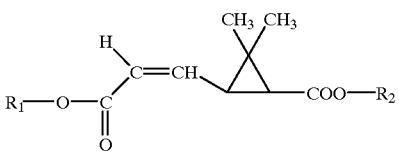
(I)

wherein:

R$_1$ is an alkyl group having a chain or branched chain of 1 to 4 carbon atoms; and R$_2$ is a group represented by the following general formulae II, III or IV;

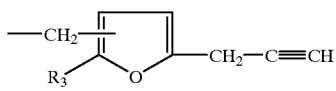
(II)

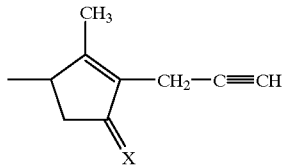
(III)

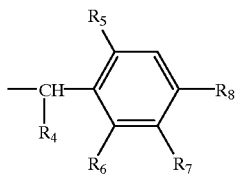
(IV)

wherein:

R$_3$ is a hydrogen atom or a methyl group;

X is an oxygen atom or a methylidene group;

R$_4$ is a hydrogen atom or an ethynyl group;

R$_5$ and R$_6$ are alike or differently selected from the group consisting of hydrogen, fluorine, chlorine atoms or methyl group;

R$_7$ is a hydrogen atom or a trifluoromethyl group;

R$_8$ is selected from the group consisting of propargyl, methoxymethyl or methylthio groups; or R$_7$ and R$_8$ may combine with each other to form a methylenedioxy chain.

Further the present invention in a twelveth embodiment relates to the insecticides and the insect proofing agents of the eleventh embodiment which contain a novel derivative of an ester of carboxylic acid, wherein the portion of cyclopropanecarboxylic acid has 1R, cis structure and the double bonds have a steric structure of Z configuration.

Each of a thirteeth embodiment to a nineteeth embodiment of the present invention relates to the insecticides and the insect proofing agents of the eleventh embodiment or the twelveth embodiment that contain a novel derivative of an ester of carboxylic acid which is represented by any one of the following formulae from V to XI.

OPERATION

According to the first embodiment of the present invention, there are provided novel and useful derivatives of esters of carboxylic acids represented by the general formula I. The compounds having the general formula I are novel compounds which are solid or liquid at room temperature and normally easy to dissolve in an organic solvent.

According to the second embodiment of the invention, there are provided the compounds of the first embodiment wherein the portion of cyclopropanecarboxylic acid has 1R, cis structure and the double bonds have a steric structure of Z configuration.

According to the third embodiment to the ninth embodiment of the invention, there are provided particularly useful compounds among the compounds of the first embodiment or the second embodiment.

According to the tenth embodiment of the invention, there are provided processes for efficiently manufacturing novel and useful derivatives of esters of carboxylic acids represented by the general formula I.

According to the eleventh embodiment of the invention, there are provided useful insecticides and insect proofing agents which contain novel derivatives of esters of carboxylic acids represented by the general formula I.

When the compounds of the present invention are applied in practice, they may be used without other ingredients blended, but generally they are used with a carrier compounded so that they will become easy to use as an insecticide and an insect proofing agent.

Insecticides and insect proofing agents for application include, for example, emulsifiable concentrate, oil solution, dust, water-dispersible powder and aerosol. They can be formulated by a well-known method in the art in a manner where the above compounds are added with adjuvants such as emulsifier, dispersant, solvent, stabilizer, etc.; solid carriers; liquid carriers; propellants, etc. according to need.

The above compounds are also used with wood flour and other appropriate base materials mixed for an insecticide and an insect proofing agent as a fumigant like a mosquito-coil. Further, when the above compounds are dissolved in an appropriate organic solvent to be absorbed by a mount or dissolved in an appropriate solvent to be absorbed by a liquid absorption wick, then are evapotranspired while heated with a suitable heating unit, that is, when they are used for an electric mosquito-repellent, they have the same efficacy as in the case of a mosquito repelling fumigant.

The insecticides and insect proofing agents of the present invention are effective against sanitary insect pests such as flies, mosquitos, cockroaches, house dust mites, etc.; clothing insect pests such as *Tinea translucens*, Dermestidae, etc.; stored grain insect pests such as *Sitophilus zeamais*, etc.; and moreover, hemipterous injurious insects such as *Myzus persicae, Aphis gossypii, Nephotettix cincticeps*, Delphacidae, Pentatomidae, etc.; lepidopteran injurious insects such as *Pieris rapae crucivora, Plutella xylostella, Mamestra brassicae*, Tortricidae, Carposinidae, etc.; coleopteran injurious insects such as scarab beetles, Chrysomelidae, Curculionidae, etc.; dipteran injurious insects such as Chironomidae, Agromyzidae, etc.; orthopteran injurious insects such as *Oxya yezoensis*. They are also effective against injurious insects which are resistant to organophosphorous insecticides and carbamate pesticides.

Further use of synergist such as N-octylbicycloheptenedicarboxyimide (trade name MGK-264), a mixture of N-octylbicycloheptenedicarboxyimide and arylsulfonate (trade name MGK-5026), Synepirine 500, octachlorodipropyl ether, piperonyl butoxide etc. makes it possible to much more heighten the efficacy of the insecticides and insect proofing agents of the present invention. Still further mixture of the other insecticidal and insect proofing ingredients, for example, organophosphorous insecticides such as fenitrothion, DDVP, diazinon, propaphos, pyridaphenthion, etc., carbamate pesticides such as NAC, MTMC, BPMC, metoxadiazone, etc., pyrethroid insecticides currently in use such as pyrethrin, allethrin, phthalthrin, furamethrin, phenothrin, permethrin, cyphenothrin, ethofenprox, etc., organosilicon compounds such as silafluofen, etc., benzoylurea compounds such as flufenoxuron, Chlorf luazuron, etc., chloronicotinyl compounds such as imidacloprid, acetamiprid, etc., hydrazine compounds such as tebufenozide, etc., nereistoxin insecticides such as cartap, thiocyclam, etc.; and still other ingredients such as miticides; fungicides; nematocides; herbicides; plant growth regulator; fertilizer; etc. with the insecticides and insect proofing agents of the present invention makes it possible to obtain an effective and multipurpose compositions, to save labor and to expect a synergistic effect between chemicals.

According to the twelvlth embodiment of the invention, there are provided more useful insecticides and insect proofing agents because used as an active ingredient of insecticides and insect proofing agents are novel derivatives of esters of carboxylic acids of the elevnth embodiment wherein the portion of cyclopropanecarboxylic acid has 1R, cis structure and the double bonds have a steric structure of Z configuration in.

According to the thirteenth embodiment to the nineteeth embodiment of the invention, there are provided further more useful insecticides and insect proofing agents because especially useful compounds among those of the eleventh embodiment or the twelvth embodiment are used as an active ingredient of insecticides and insect proofing agents.

Examples of the process for synthesizing a novel derivative of an ester of carboxylic acid according to the present invention are shown as follows:

SYNTHESIS EXAMPLE

Synthesis Example 1 Synthesis of Compound 1

2.7 g of 5-propargyl-2-furylmethyl alcohol and 2.3 g of triethylamine were dissolved in 40 ml of dichloromethane, and 4.8 g of 2,2-dimethyl-3-(3-methoxy-3-oxo-1-propenyl) cyclopropanecarboxylic chloride was added to the solution while the solution was being cooled with ice. Then the reaction solution was warmed to room temperature, and it was washed with 50 ml of 2% hydrochloric aqueous solution after agitated at room temperature for 3 hours and again washed with 50 ml of saturated brine. After the organic layer was dried with magnesium sulfate, dichloromethane was removed by vacuum concentration and the resultant oily material was refined on a silica gel column chromatography (eluent; ethyl acetate: n-hexane=1:40). Thus 6.1 g of colorless 5-propargyl-2-furylmethyl 2,2-dimethyl-3-(3-methoxy-3-oxo-1-propenyl) cyclopropanecarboxylate was obtained.

IR 3300cm$^{-1}$ (—CH$_2$—C—≡CH), 1730 cm$^{-1}$(—COO—)

Synthesis Example 2 Synthesis of Compound 3
(the acid portion has 1R, cis structure and the steric structure is Z configuration)

4.0 g of 1R, cis-2,2-dimethyl-3-[1-(ΔZ)-3-methoxy-3-oxopropenyl] cyclopropanecarboxylic acid and 3.0 g of (S)-2-methyl-3-propargyl-4-oxo-2-cyclopentene-1-ol were dissolved in 50 ml of dichloromethane, and a solution of 4.3 g of dicyclohexylcarbodiimide and 0.2 g of 4-dimethylaminopyridine dissolved in 40 ml of dichloromethane was added to the above solution while cooled with ice. After agitated at room temperature for 12 hours, the solution was filtered and the filtrate was concentrated by vacuum distillation. The residual material was refined on a silica gel column chromatography (eluent; ethyl acetate: n-hexane=1:20). Thus 6.0 g of colorless (S)-2-methyl-3-propargyl-4-oxo-2-cyclopentene-1-yl 1R, cis-2,2-dimethyl-3-[1-(ΔZ)-3-methoxy-3-oxopropenyl] cyclopropanecarboxylate was obtained.

IR 3300cm$^{-1}$ (—CH$_2$—C≡CH), 1730 cm$^{-1}$ (—COO—)

Synthesis Example 3 Synthesis of Compound 6

4.1 g of 2,2-dimethyl-3-(3-methoxy-3-oxo-1-propenyl) cyclopropanecarboxylic acid was dissolved in 50 ml of acetone, and 4.3 g of 4-methoxymethylbezylbromide was added to the solution. Next 2.4 g of triethylamine was added to the solution and underwent reaction at 60–80° C. for 3 hours while agitated, after which ether was added. After the ether solution was fully washed with diluted hydrochloric acid, sodium hydrogencarbonate aqueous solution and brine, it was dried with mirabilite. Ether was distilled under reduced pressure, and 6.3 g of 4-methoxymethylbezyl 2,2-dimethyl-3-(3-methoxy-3-oxo-1-propenyl) cyclopropanecarboxylate was obtained.

IR 1740 cm$^{-1}$(—COO—)

In order to clarify how excellent the insecticides and insect proofing agents containing novel derivatives of esters of carboxylic acids according to the present invention, a number of embodiments of the present invention and results of efficacy test of the present invention will now be explained below.

EXAMPLE 1

White kerosene was added to 0.2 parts of the compound (1) of the present invention to become 100 parts altogether, and 0.2% of oil solution was obtained.

EXAMPLE 2

White kerosene was added to 0.2 parts of the compound (2) of the present invention and 0.8 parts of piperonyl butoxide to become 100 parts altogether, and oil solution was obtained.

EXAMPLE 3

10 parts of sorpol SM-200 (trade name of Toho Chemical Industry Co., Ltd.) and 70 parts of xylol were added to 20 parts of the compound (3) of the present invention, and mixed and dissolved while agitated. Then 20% of emulsifiable concentrate was obtained.

EXAMPLE 4

0.4 parts of the compound (4) of the present invention and 1.5 parts of octachlorodipropyl ether were dissolved in 28 parts of refined kerosene, and the solution was filled into an aerosol container. Then valve portion was attached to the container, and 70 parts of propellant were filled in via the valve portion under pressure. Thus aerosol was obtained.

EXAMPLE 5

0.5 parts of the compound (5) of the present invention and 0.5 g of BHT were mixed uniformly with 99.0 g of the base material for mosquito-coil such as pyrethrum, wood flour, starch, etc., and mosquito-coil was obtained by a well-known method.

EXAMPLE 6

0.3 parts of the compound (8) of the present invention and 99.7 parts of clay were well ground and mixed, and 0.3% of dust was obtained.

EXAMPLE 7

40 parts of the compound (10) of the present invention, 35 parts of diatom aceous earth, 20 parts of clay, 3 parts of laurylsulfonate and 2 parts of carboxymethyl cellulose were ground and mixed, and water-dispersible powder was obtained.

Efficacy Test Example 1

Percentage of knocked-down house flies was obtained of each of 0.2% white kerosene solution of the compound of the present invention (A), 0.2% synepirine 500, 0.8% white kerosene solution of the compound of the present invention (B), and 0.2% white kerosene solution of each of phthalthrin and phenothrin to calculate the relative effective concentration of the test chemicals, after which motality of each chemical after 24 hours was obtained as shown in Table 1.

The numbers in parentheses indicate the motality after 24 hours.

TABLE 1

| | Test chemicals | A | B |
|---|---|---|---|
| Present invention | Compound 1 | 2.46 (100) | 4.13 (100) |
| | Compound 2 | 2.29 (100) | 3.90 (100) |
| | Compound 3 | 2.15 (100) | 3.89 (100) |
| | Compound 4 | 2.20 (100) | 4.05 (100) |
| | Compound 5 | 2.02 (100) | 3.87 (100) |
| | Compound 6 | 2.14 (100) | 3.92 (100) |
| | Compound 7 | 2.08 (100) | 3.78 (100) |
| | Compound 8 | 1.93 (100) | 3.61 (100) |
| | Compound 9 | 2.06 (100) | 3.83 (100) |
| | Compound 10 | 1.91 (100) | 3.44 (100) |
| | Compound 11 | 2.40 (100) | 4.06 (100) |
| | Compound 12 | 2.25 (100) | 3.85 (100) |
| | Compound 13 | 2.12 (100) | 3.82 (100) |
| | Compound 14 | 2.17 (100) | 3.96 (100) |
| | Compound 15 | 1.94 (100) | 3.50 (100) |
| | Compound 16 | 1.96 (100) | 3.53 (100) |
| | Compound 17 | 2.01 (100) | 3.74 (100) |
| | Compound 18 | 2.19 (100) | 3.88 (100) |
| | Compound 19 | 2.41 (100) | 4.06 (100) |
| Comparative examples | Phthalthrin | 1.00 (34) | — |
| | Phenothrin | 0.43 (98) | — |

It was proved from the results of the test that the compounds of the present invention have a knockdown effect (fast-acting property) exceeding phthalthrin, which is known as a knockdown agent, and a lethal effect identical with or exceeding phenothrin, which is known as a kill agent, and therefore they are extremely useful as an active ingredient of insecticides and insect proofing agents.

It was also proved that compounding synepirine 500, which is traditionally synergist of pyrethroid, heightens the insecticidal and insect proofing effects thereof.

Efficacy Test Example 2

About 50 images of Culex pipiens pallens were set free in a (70 cm)$^2$ of glass chamber, after which a small-sized electric fan (the blade was 13 cm in diameter) was provided in the chamber and turned on. When 0.1 g of mosquito-coil containing the compounds (1), (5), (8), (10), (13) and (17) which were obtained according to Example 5 were lighted and put into the chamber, 80% or more of Culex pipiens pallens were knocked down within 30 minutes and after one day 80% or more of the knocked down Culex pipiens pallens were killed.

Similarly, each of 40 mg of the compound (2), (4), (7), (14) and (19) of the present invention with which 2.2×3.5 cm of pulp mat was soaked were transpired by heating with an electric mosquito-repellent having an about 170° C. of radiating plate. As a result, a high mosquito proofing effect was obtained just like in the case of the case of a mosquito-coil.

Efficacy Test Example 3

Dust of each of the compounds (3), (5), (8), (9), (12) and (16) of the present invention according to Example 6 was uniformly applied to the bottom surface of a Petri dish having a diameter 14 cm at a rate of 2 g/m$^2$, and butter was applied to the wall surface of the Petri dish leaving the portion 1cm from the bottom unapplied. Then 10 images of German cockroach, as a group, were set free in the Petri dish to touch the dust for 30 minutes, after which they were moved to another container. After 3 days, 80% or more of the cockroach were killed by any of the dust.

Efficacy Test Example 4

Each solution of the emulsifiable concentrate containing the compounds (2), (6), (9), (10), (15) and (18) of the present invention according to Example 3 was diluted with water by 1000 times, and applied at a rate of 100 l/tan (about 10.1 l/a) to a Japanese radish field at 5 to 6-leaf stage where Myzus persicae broke out. From the survey of parasitism rate after 2 days, it was found that the ratio at every field was reduced to below 1/10 of that before applying the solution.

Efficacy Test Example 5

8.0 g of azodicarbonamide which is an organic blowing agent and 1.0 g of adjuvant such as caking additive, etc. were added to 1.0 g of each of the compounds (1), (3), (8), (11) and (16), after which they were well mixed and filled into aluminum bags. When a bag of this fumigant which is in the form of dust-grain was heated to about 250° C. with a heater in a 6 tatami-mats room, the ingredient was diffused over the whole room via holes made in the aluminum bags so that smoke could pass through them. The fumigant was effective in controlling not only cockroaches, fleas and bedbugs but mites in house dust such as Dermato phagoides farinae and Tyrophagus putrescentiae.

EFFECTS OF THE INVENTION

Novel derivatives of esters of carboxylic acids of the first embodiment of the invention represented by the general formula I are useful compounds; particularly, compounds of the second embodiment, of which portion of cyclopropanecarboxylic acid has 1R, cis structure and the double bonds have a steric structure of Z configuration, and selected compounds of the third embodiment to the ninth embodiment have a high practical use.

According to the process of the tenth embodiment, novel and useful derivatives of esters of carboxylic acids represented by the above general formula I are obtained.

The insecticides and insect proofing agents containing novel derivatives of esters of carboxylic acids of the eleventh embodiment, which are represented by the above general formula I, have both a fast-acting property and a lethal effect and in addition their toxicity to warm-blooded animals are low; therefore, they are much more useful than those containing pyrethroids currently in use. Particularly, the insecticides and insect proofing agents of the twelveth embodiment, which contain compounds of which portion of cyclopropanecarboxylic acid has 1R, cis structure and the double bonds have a steric structure of Z configuration, and the insecticides and insect proofing agents of the thirteeth embodiment to the nineteeth embodiment, which contain selected compounds, have a high practical use.

What is claimed is:

1. A derivative of esters of carboxylic acids represented by the general formula I:

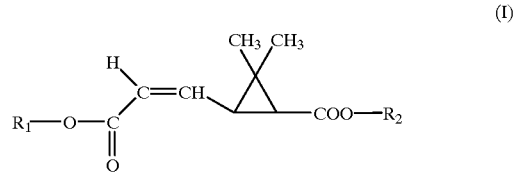

wherein:

$R_1$ is an alkyl group having a chain or branched chain of 1 to 4 carbon atoms; and $R_2$ is a group represented by the following general formula IV:

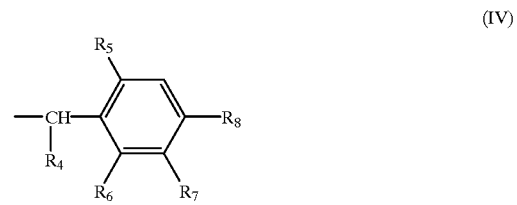

wherein:

$R_4$ is a hydrogen atom or an ethynyl group;

$R_5$ and $R_6$ are alike or differently selected from the group consisting of hydrogen and a methyl group;

$R_7$ is a hydrogen atom; and $R_8$ is selected from the group consisting of propargyl, methoxymethyl and methylthio groups.

2. The derivative of esters of carboxylic acids according to claim 1 wherein the portion of cyclopropanecarboxylic acid has 1R, cis structure, and the double bond has a steric structure of Z configuration.

3. The derivative of esters of carboxylic acids according to claim 1 or claim 2 which has the following formula VIII:

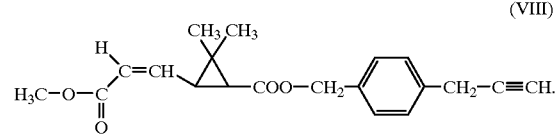

4. The derivative of esters of carboxylic acids according to claim 1 or claim 2 which has the following formula IX:

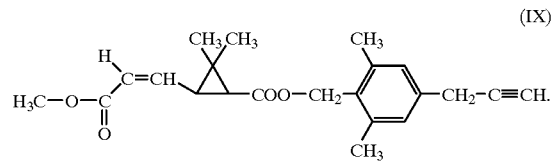

5. The derivative of esters of carboxylic acids according to claim 1 or claim 2 which has the following formula X:

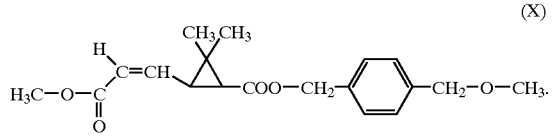

6. The derivative of esters of carboxylic acids according to claim 1, wherein $R_8$ is a methylthio group.

7. An insecticidal composition comprising a carrier and a derivative of esters of carboxylic acids represented by the general formula I:

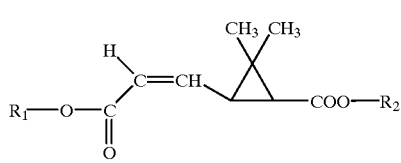

wherein:
- $R_1$ is an alkyl group having a chain or branched chain of 1 to 4 carbon atoms; and
- $R_2$ is a group represented by the following general formula IV:

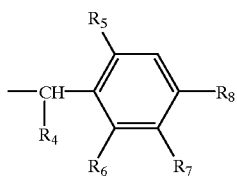

wherein:
- $R_4$ is a hydrogen atom or an ethynyl group;
- $R_5$ and $R_6$ are alike or differently selected from the group consisting of hydrogen and a methyl group;
- $R_7$ is a hydrogen atom; and
- $R_8$ is selected from the group consisting of propargyl, methoxymethyl and methylthio groups, a hydrogen atom.

8. The insecticidal composition according to claim 7 comprising a compound wherein the portion of cyclopropanecarboxylic acid having 1R, cis structure and the double bond has a steric structure of Z configuration.

9. The insecticidal composition according to claim 7 or claim 8 comprising contain the compound represented by he following formula VIII:

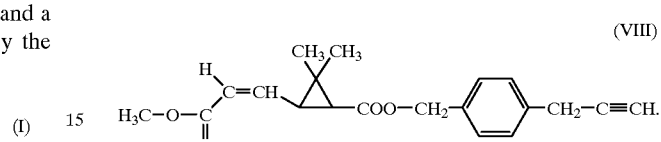

10. The insecticidal composition according to claim 7 or claim 8 comprising the compound represented by the following formula IX:

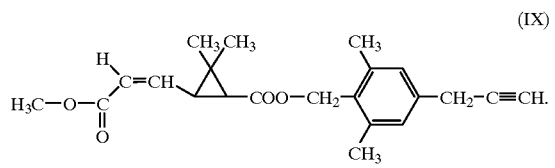

11. The insecticidal composition according to claim 7 or claim 8 comprising the compound represented by the following formula X:

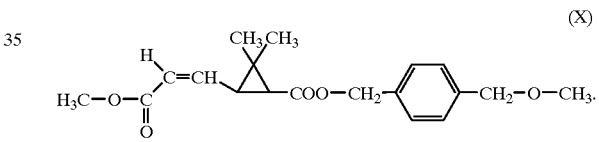

12. The insecticidal composition according to claim 7, wherein $R_8$ is a methylthio group.

* * * * *